(12) United States Patent
Cornish et al.

(10) Patent No.: US 8,480,597 B2
(45) Date of Patent: Jul. 9, 2013

(54) COLOR CODED GUIDE WIRE AND METHODS OF MAKING SAME

(75) Inventors: Wayne E. Cornish, Fallbrook, CA (US); Travis R. Yribarren, Campbell, CA (US); Carl P. Frick, Laramie, WY (US); Jessica M. Saenz, Lake Elsinore, CA (US); Emmanuel C. Biagtan, Temecula, CA (US); Pablito Buan, Temecula, CA (US); David H. Burkett, Temecula, CA (US); John J. Nelson, III, New Haven, CT (US); Robert J. Peralta, Murrieta, CA (US); Michelle E. Alexander, Murrieta, CA (US); Arthur R. Tyre, Murrieta, CA (US); John A. Simpson, Carlsbad, CA (US)

(73) Assignee: Abbott Laboratories, Santa Clara, CA (US)

( * ) Notice: Subject to any disclaimer, the term of this patent is extended or adjusted under 35 U.S.C. 154(b) by 247 days.

(21) Appl. No.: 12/880,465

(22) Filed: Sep. 13, 2010

(65) Prior Publication Data
US 2012/0065622 A1    Mar. 15, 2012

(51) Int. Cl.
*A61M 25/09*    (2006.01)
(52) U.S. Cl.
USPC ............................................ 600/585; 600/434
(58) Field of Classification Search
USPC .................... 600/585; 604/264; 427/500, 501
See application file for complete search history.

(56) References Cited

U.S. PATENT DOCUMENTS

| | | | |
|---|---|---|---|
| 4,538,622 A | 9/1985 | Samson et al. | |
| 4,748,986 A | 6/1988 | Morrison et al. | |
| 5,135,503 A | 8/1992 | Abrams | |
| 5,341,818 A | 8/1994 | Abrams et al. | |
| 5,345,945 A | 9/1994 | Hodgson et al. | |
| 5,636,641 A | 6/1997 | Fariabi | |
| 6,585,755 B2 * | 7/2003 | Jackson et al. | 623/1.15 |
| 6,605,049 B1 * | 8/2003 | Wagner et al. | 600/585 |
| 7,411,008 B2 * | 8/2008 | Tucker et al. | 523/160 |
| 7,524,281 B2 * | 4/2009 | Chu et al. | 600/37 |
| 7,811,623 B2 * | 10/2010 | Nesbitt | 427/2.1 |
| 8,231,926 B2 * | 7/2012 | Nesbitt | 427/2.1 |
| 8,231,927 B2 * | 7/2012 | Nesbitt et al. | 427/2.1 |
| 8,349,249 B2 * | 1/2013 | Wachter et al. | 420/427 |
| 2005/0076831 A1 * | 4/2005 | Gilliard et al. | 118/301 |
| 2005/0209533 A1 * | 9/2005 | Lorenz | 600/585 |
| 2006/0015039 A1 * | 1/2006 | Cassidy et al. | 600/585 |
| 2009/0048537 A1 * | 2/2009 | Lydon et al. | 600/585 |
| 2009/0162531 A1 * | 6/2009 | Nesbitt | 427/2.12 |
| 2009/0181156 A1 * | 7/2009 | Nesbitt et al. | 427/2.1 |
| 2009/0211909 A1 * | 8/2009 | Nesbitt | 204/487 |

OTHER PUBLICATIONS

Kikuti, E., et al., "Chemical and Electrochemical Coloration of Stainless Steel and Pitting Corrosion Resistance Studies," Journal of the Brazilian Chemical Society, May 17, 2004, pp. 472-480, vol. 15, No. 4, Sociedude Brasileira de Quimica, Brazil.

(Continued)

*Primary Examiner* — Sean Dougherty
(74) *Attorney, Agent, or Firm* — Fulwider Patton LLP

(57) ABSTRACT

A color coding is applied to medical guide wires by coloring portions of the guide wire to distinguish similar guide wires and guide wire portions from a particular manufacturer. The metallic elongate core can be colored using various methods such as electrochemical processes, sputtering, electroplating, and laser inducing microstructures to alter the surface characteristics of the elongate metallic core. Alternatively, the outer layer of the guide wire can be color coded by using non-standard colors or by introducing a colored band on the guide wire.

38 Claims, 7 Drawing Sheets

OTHER PUBLICATIONS

Vorobyev, A.Y., et al., "Colorizing metals with femtosecond laser pulses," Applied Physics Letters 92, Jan. 31, 2008:041917-1 to 041917-3.

Colored Finishes (Brochure), www.bmfinishers.com/stainless_steel.html, Feb. 8, 2008.

Bluing (steel), wikipedia.org/wiki/Bluing, Wikipedia, Feb. 8, 2008, 4 pages.

University of Rochester, "Researchers Create Gold Aluminum, Black Platinum, Blue Silver," Press Release, Mar. 13, 2008, 2 pages, Rochester, New York.

* cited by examiner

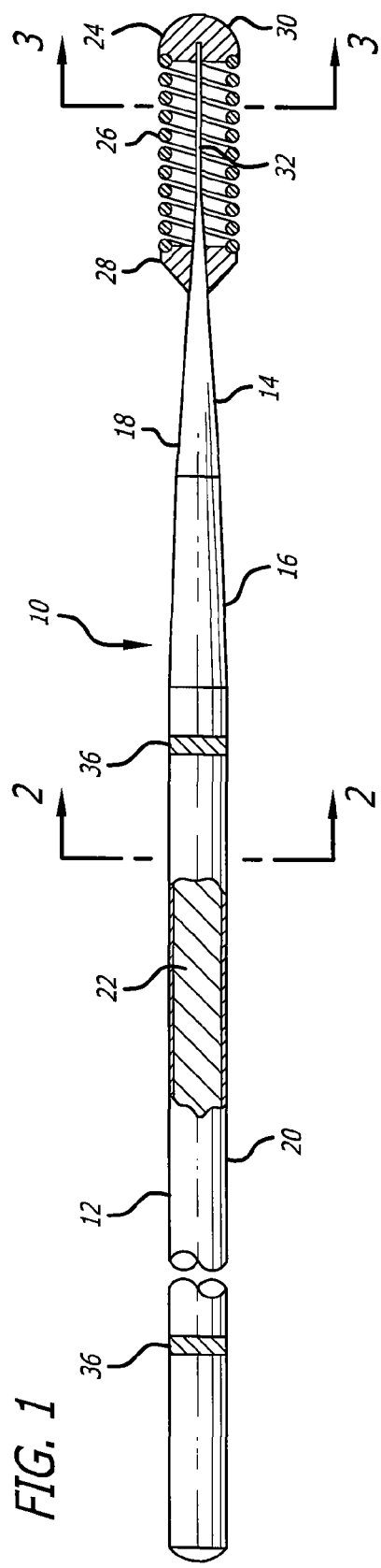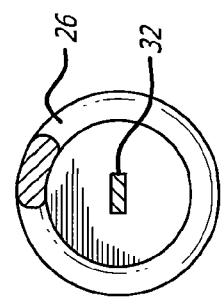

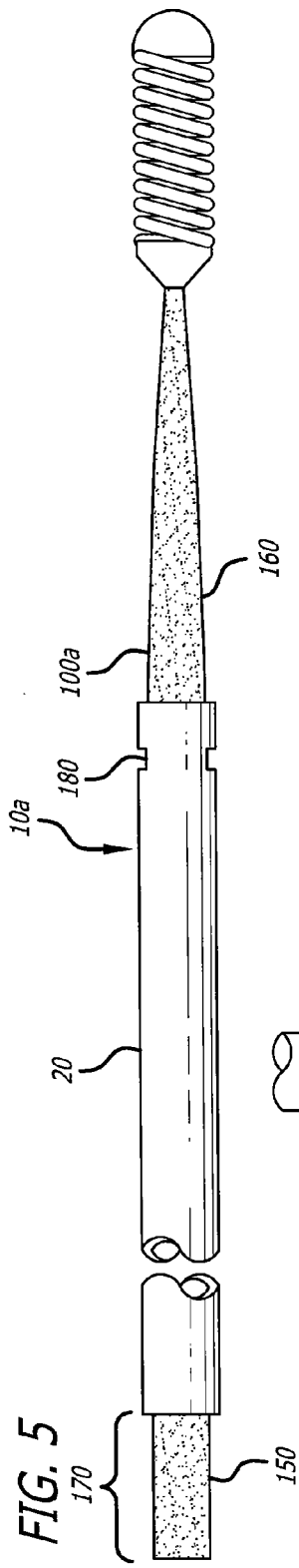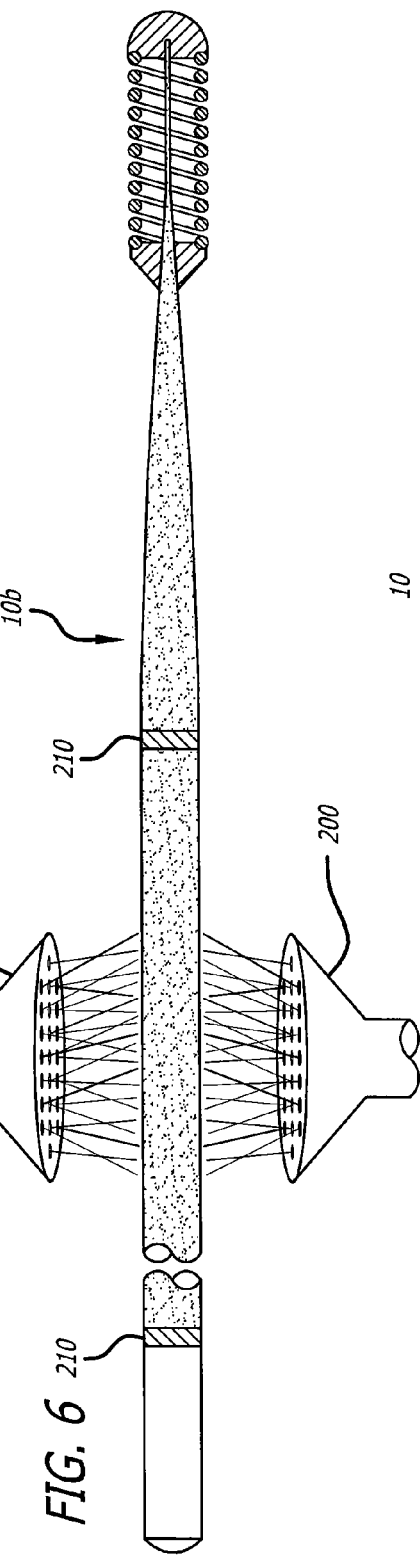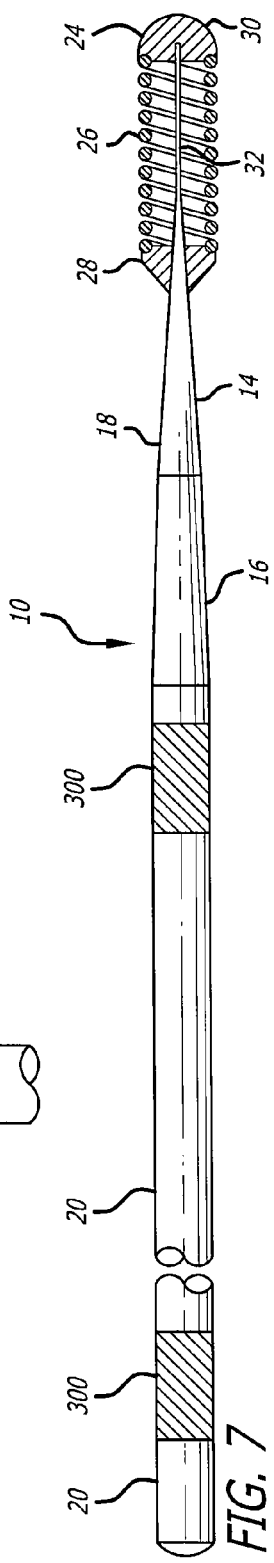

COLOR CODED GUIDE WIRE AND METHODS OF MAKING SAME

BACKGROUND

This invention relates to the field of guide wires for advancing intraluminal devices such as stent delivery catheters, balloon dilatation catheters, atherectomy catheters and the like within a patient's body, such as within a patient's vasculature.

In a typical percutaneous procedure in a patient's coronary system, a guiding catheter having a preformed distal tip is percutaneously introduced into a patient's peripheral artery, e.g. femoral, radial or brachial artery, by means of a conventional Seldinger technique and advanced therein until the distal tip of the guiding catheter is seated in the ostium of a desired coronary artery. There are two basic techniques for advancing a guide wire into the desired location within the patient's coronary anatomy, the first is a preload technique which is used primarily for over-the-wire (OTW) devices and the bare wire technique which is used primarily for rail type systems. With the preload technique, a guide wire is positioned within an inner lumen of an OTW device such as a dilatation catheter or stent delivery catheter with the distal tip of the guide wire just proximal to the distal tip of the catheter and then both are advanced through the guiding catheter to the distal end thereof. The guide wire is first advanced out of the distal end of the guiding catheter into the patient's coronary vasculature until the distal end of the guide wire crosses the arterial location where the interventional procedure is to be performed, e.g. a lesion to be dilated or a dilated region where a stent is to be deployed.

The catheter, which is slidably mounted onto the guide wire, is advanced out of the guiding catheter into the patient's coronary anatomy over the previously introduced guide wire until the operative portion of the intravascular device, e.g. the balloon of a dilatation or a stent delivery catheter, is positioned across the arterial location. Once the catheter is in position with the operative means located within the desired arterial location, the interventional procedure is performed. The catheter can then be removed from the patient over the guide wire. Usually, the guide wire is left in place for a period of time after the procedure is completed to ensure re-access to the arterial location if it is necessary. For example, in the event of arterial blockage due to dissected lining collapse, a rapid exchange type perfusion balloon catheter such as described and claimed in U.S. Pat. No. 5,516,336 (McInnes et al.), can be advanced over the in-place guide wire so that the balloon can be inflated to open up the arterial passageway and allow blood to perfuse through the distal section of the catheter to a distal location until the dissection is reattached to the arterial wall by natural healing.

With the bare wire technique, the guide wire is first advanced by itself through the guiding catheter until the distal tip of the guide wire extends beyond the arterial location where the procedure is to be performed. Then a rail type catheter, such as described in U.S. Pat. No. 5,061,273 (Yock) and the previously discussed McInnes et al. which are incorporated herein by reference, is mounted onto the proximal portion of the guide wire that extends out of the proximal end of the guiding catheter outside of the patient. The catheter is advanced over the guide wire, while the position of the guide wire is fixed, until the operative means on the rail type catheter is disposed within the arterial location where the procedure is to be performed. After the procedure the intravascular device may be withdrawn from the patient over the guide wire or the guide wire advanced further within the coronary anatomy for an additional procedure.

Conventional guide wires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon secured to the distal extremity of the core member, extends through the flexible body and is secured to the distal end of the flexible body by soldering, brazing or welding which forms a rounded distal tip. Torquing means are provided on the proximal end of the core member to rotate, and thereby steer, the guide wire while it is being advanced through a patient's vascular system.

Further details of guide wires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.) and U.S. Pat. No. 5,636,641 (Fariabi) which are hereby incorporated herein in their entirety by reference thereto.

Guide wires are typically designed for specific applications that call for varying stiffness, diameter, lubricity, tactile feedback, and lengths. However, there is little in the way of distinguishing characteristics between different guide wires, particularly those with a stainless steel core and a standard polymer body. The structure and design of guide wires results in a similarity in the appearance of substantially all models and brands of guide wires. This makes it difficult to establish brand recognition among guide wire manufacturers and presents problems when selecting guide wires for a particular purpose since they all appear alike. For example, in a bifurcation stent delivery procedure, it is common for the physician to place one guide wire within the side branch of the bifurcation and another guide wire within the main branch of the bifurcation. In such circumstances, it is customary for the physician to use some personal method of distinguishing the guide wires, such as always placing the side guide wire to the right of the main guide wire, placing a cloth on one guidewire as a marker, or another similar methodology. This personal methodology is susceptible to error. Furthermore, distinguishing brand recognition is difficult in this market since most guide wires appear similar, even if performance differs from manufacturer to manufacturer.

SUMMARY OF THE INVENTION

The present invention seeks to overcome the shortcomings of the indistinguishable appearance of guide wires by constructing a system and method for color coding various guide wires to distinguish one mode or brand from another. In a first embodiment of the present invention, the guide wire core is subjected to a coloring process such as electrochemically altering the color of the steel core to produce a steel core having a distinct hue. Electrochemical processes can produce gold, bronze, purple, blue, red, black, and green surfaces on the core of the guide wire. The stainless steel wire is immersed in a heated acid bath and electrical current is applied, thereby thickening the transparent chromium oxide film. This has the dual effect of protecting the stainless steel core from oxidation and corrosion, and also alters the way light is reflected by the surface. A full spectrum of colors are available, and the colors will not fade. The guide wire can be colored with or without a PTFE coating, and a silicone-based protective layer can be applied over the colored core to enhance lubricity. Where a PTFE coating is applied, the coating can be transparent to reveal the underlying colored core section of the guide wire, or the PTFE coating can be opaque and applied in sections to reveal windows or sections of the color coded core. The color coded sections or windows can also be used as markers along the guide wire to assist with the placement of the guide wire. The electrochemical process can be applied prior to assembly of the guide wire, or it can be applied to a selected portion of a fully constructed guide wire assembly. Alternatively, the guide wire can be coded with PTFE with a non-standard color such as white, blue, yellow or gold among other colors. In this manner, the PTFE coating can be used to color code the guide wires. The PTFE coating may be applied from either a spray process where designated sections can be easily masked to coat the exterior with one or more designated colors, or a continuous reel-to-reel coating process can be used.

In another embodiment of the present invention, a colored band is positioned on the guide wire between the PTFE location and a proximal docking extension. This colored band can be any desired length, with a preferred length between 1 to 20 centimeters. The band can be applied by one of many processes, including an extrusion process of applying a thin coating onto a non-continuous length of wire. For example, a colored polymer with high adhesion characteristics to stainless steel is extruded onto a selected section of the guide wire, where the polymer is of a color that particularly stands out from standard green PTFE, such as white, yellow, gold, or teal. A laser treatment can be applied to the guide wire prior to the extrusion process to remove a portion of the PTFE, and then a polishing or grinding process may be used to roughen the surface of the bare wire core for better adhesion. A silane coating may also be applied to further promote polymer adhesion. Choice of polymers can include, but are not limited to, melt-processable fluoropolymers and polyurethanes. In an alternative embodiment, an extrusion die assembly may be modified so that the molten polymer flows into a cavity between the die and the wire core. Once cooled, the guide wire is removed from the extrusion assembly.

In another embodiment of the present invention, a guide wire is color coded by applying an ultra-short, intense laser beam (e.g. femtosecond laser) that forms nanostructures on the guide wire. The nanostructures absorb and reflect light differently than the core guide wire material, thereby producing a colored guide wire section. The laser forms nanostructures such as pits, globules, and strands that modify the material's optical characteristics. Variation of the laser's intensity, pulse length, and number of pulses can control the size and shape of these nanostructures, and thus how they reflect light. Metals with a silver appearance can be modified to appear gold, iridescent, and other colors.

In another embodiment, a guide wire assembly includes a guide wire having a tapered proximal end for receiving a color coded tubular sleeve that slides over the tapered portion and is removably lodged onto the tapered section. In this embodiment, the guide wire typically is used with a dock extension wire and has a undulating wire at its proximal end that has been formed by grinding the proximal section of the guide wire. The undulating portion, sometimes referred to as a "coined" portion, has an undulating structure that gradually tapers to the core wire diameter, typically 0.3556 mm (0.014 inch). Other guide wire diameters also are contemplated. Further, the color coded tubular sleeve slides over the undulating portion or coined portion of the guide wire and firmly lodges onto the tapered portion of the proximal end of the guide wire. No other adhesive or laser welding is required to removably attach the tubular sleeve onto the tapered portion. In use, when two guide wires are used simultaneously in a patient, the physician will simply remove one of the color coded tubular sleeves by pinching the tubular sleeve with his/her fingers and pulling the tubular sleeve proximally off of the tapered portion of the proximal end of the guide wire. Thus, the physician can distinguish between the two guide wires since one will have no color coded tubular sleeve, while the other guide wire still has a color coded tubular sleeve.

BRIEF DESCRIPTION OF THE DRAWINGS

FIG. 1 is a perspective view, partially cut away, of an embodiment of a guide wire of the present invention.

FIG. 2 is a cross-sectional view of the guide wire of FIG. 1 taken along lines 2-2.

FIG. 3 is a cross-sectional view of the guide wire of FIG. 1 taken along lines 3-3.

FIG. 5 is a perspective view of a guide wire having a colored core.

FIG. 6 is an elevated perspective view of a guide wire subjected to a spraying process.

FIG. 7 is a perspective view of another embodiment of the present invention having a colored band at a proximal end.

DETAILED DESCRIPTION OF THE PREFERRED EMBODIMENTS

Figure 4:
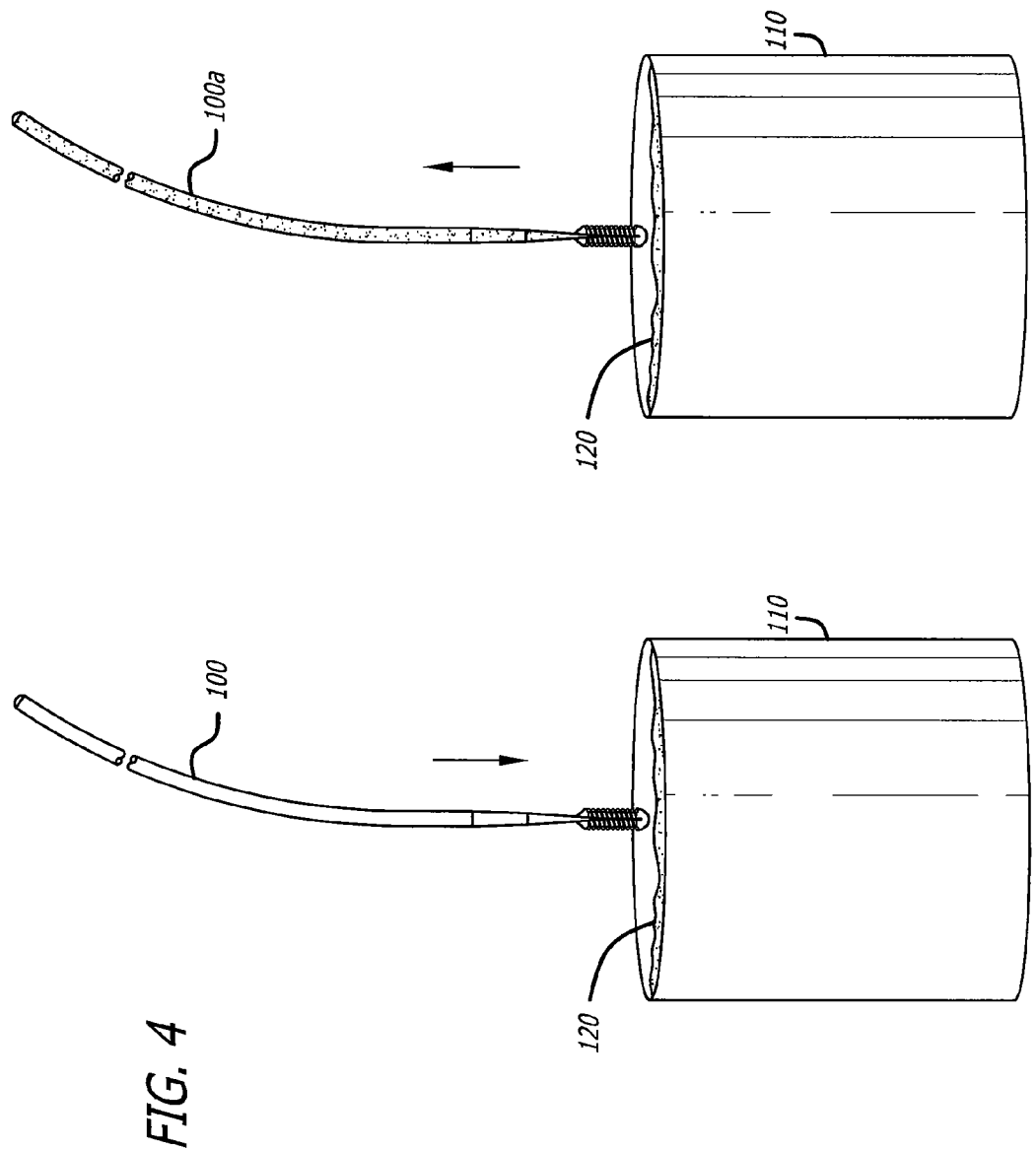
FIG. 4 is an elevated perspective view of a guide wire immersed into and extracted from an electrochemical solution.

The present invention is directed to an elongated intracorporeal device such as a guide wire having a color coding system. The color coding distinguishes similar guide wires for use in procedures where multiple guide wires are used as well as helping to select an appropriate guide wire for a single guide wire procedure. The color coding can also be used for brand recognition to distinguish one manufacturer from another. In various embodiments, the color coding can be applied to the metal core, either at a distal or proximal end, or to a flexible outer body portion of the guide wire. Various methods for implementing the color coding of the guide wires are set forth below, and the description of the color coding methods are intended to be illustrative but not limiting.

FIG. 1 is a side elevational view partially in section of one embodiment of the present invention guide wire 10. The guide wire 10 includes an elongated core having a proximal core section 12 and a distal core section 14. In this embodiment, the entire wire core is made from a single material such as stainless steel. In various alternative embodiments (not shown), the proximal core section can be made from a high strength steel while the distal core section 14 is made from a superelastic alloy such as nickel-titanium (e.g., Nitinol) or the like. The two core sections can be joined by a weld or adhesive, and/or by an interconnecting hypotube made from various materials.

Returning to FIG. 1, the guide wire 10 includes optional tapered sections 16, 18. Specifically, the present invention contemplates one or more tapered profiles at varying degrees of taper, although straight, curved, and/or stepped profiles are also contemplated. The guide wire 10 further includes a coating 20 disposed on and adhering to the wire core 22. The surface coating 20 or the surface of the wire core 22, or both, include color coding as discussed below.

The surface coating 20 may only partially cover the guide wire core 22 or may envelop the entire core altogether. The surface coating may be a low friction material such as polytetrafluoroethylene ("PTFE") that aids in positioning the guide wire 10. The coating may include positional markers 36 at the distal or proximal end to aid the practitioner in locating the end portion(s) of the guide wire 10. Toward the distal end 24 of the guide wire 10 is typically a flexible member 26. Preferably the flexible member 26 is one or more helical coils welded, bonded, soldered, or otherwise attached to the distal core section 14. In a preferred embodiment, the flexible member is made of a radiopaque material such as platinum to help provide accurate positioning of the guide wire. In the embodiment shown, the flexible member 26 is attached at its proximal end by a weld or solder mass 28 and at its distal end by a solder ball 30 or similar rounded tip. Furthermore, the guide wire 10 features a flattened distal tip 32 that extends into the solder ball 30. FIGS. 2 and 3 are cross-sectional views of the guide wire 10 taken along lines 2-2 and 3-3 of FIG. 1, respectively.

FIG. 4 shows a process in which a guide wire 100 is submerged into a container 110 having an electrochemical solution 120 therein to impart a color to the stainless steel core of the wire. It is known that stainless steel can be colored by electrochemical bathing, as well as sputtering, electroplating, and paints. In electrochemical bathing, the metal is immersed in a hot acid solution and an electrical current is applied. This thickens the transparent chromium oxide film that makes stainless steel corrosion resistant, and also changes the way light is reflected by the surface of the metal. By varying the length of the bath, the amount of current supplied, and the acidity of the solution, a full spectrum of colors may be manifested including but not limited to gold, bronze, purple, blue, red, black, and green. The color will not fade and can be applied uniformly or varied for a rainbow effect. The color can also be selectively removed by etching, polishing or engraving.

The wire 100a after being removed from the electrochemical solution 120 has its appearance changed from the silver color of stainless steel to another color. Exemplary colors include bronze, purple, blue, red, black, or green. The wire 100a can then be incorporated into a guide wire 10a (FIG. 5) by applying a flexible polymer coating 20 onto the wire such as PTFE, where the proximal 150 and distal 160 ends of the guide wire reflect the colored wire core. The PTFE coating can be applied to the entire wire core 100a, or it can be applied to all but a proximal 5 to 20 centimeters of the wire core, leaving a portion 170 of the colored wire core exposed for easy identification and differentiation. In addition, by careful removal of the PTFE coating the colored wire core can be used as the markers 180 along the guide wire 10a. Alternatively, the guide wire can be assembled first and then the electrochemical process is applied to only the proximal end 170 of an exposed portion of wire core 100a, coloring only the exposed proximal end. The color wire core can alternatively be cut into 1 to 10 centimeter lengths and attached to the proximal end of an untreated wire core. A silicone-based film may preferably be applied to enhance lubricity before the coating is applied. In addition to the change in appearance of the guide wire due to the electrochemical process, the thickening of the chromium oxide film increases the resistance to corrosion in the colored wire.

In a second embodiment of the invention, the PTFE coating that is applied to the colored wire 100a is transparent, such that the colored wire 100a can be viewed through the PTFE coating. The underlying colored wire is visible through the transparent coating for the length of the guide wire while the low friction properties of the PTFE coating are preserved. In each embodiment, a set of guide wires can be created with a spectrum of colors to distinguish different types of guide wires, or to distinguish otherwise similar guide wires from each other using the colored wire core.

As an alternative to electrochemical bathing, the wire core can be colored by plasma vapor deposition or sputtering. This process typically applies a very thin, colored ceramic or metallic coating to the surface of the wire core. A variety of colors can be obtained, including gold, black, blue, red, rose gold, silver gold, and brass. The color is stable, very uniform, and more abrasion resistant than electrochemical coloring.

In another embodiment of the present invention, the PTFE coating provides a color coding in lieu of or in addition to the color coding of the wire core. Traditionally guide wires have had PTFE coatings that are green, black, or grey. There is no apparent reason for the limitation on the colors for the PTFE coatings, but the limited colors for the coatings prevent any brand recognition and result in most guide wires having the same appearance. Applying a non-standard color coating of the fluoropolymer layer, such as blue, white, yellow, or gold, distinguishes these wires from others existing in the market. Color coding the PTFE layer allows for brand recognition of a manufacturer and can be used to visually distinguish a particular type of guide wire or distinguish between two similar guide wires used in the same procedure. The non-standard color PTFE coating replaces the full length standard PTFE coating on the guide wire, making all portions of the guide wire easily distinguishable based on the color coding.

Alternatively, the PTFE (or fluoropolymer coating) may be applied from a solution that is spray, dip, or reel-to-reel coded. Here, spray coating may be the most practical method since designated sections can be more easily masked and coded with different colored sections. In FIG. 6, a colored spray coating is applied to a wire 10b as it passes between two nozzles 200 to color the guide wire with a nonstandard color such as blue, white, yellow, or gold. Masks 210 can be used to form non-colored portions on the guide wire, which when removed presents portions of original colored guide wire that can then be used as markers or for other distinguishing purposes. The colored coating can be applied to the full length of the guide wire, or to the proximal section of the guide wire between a docking extension and a proximal end. In the latter example, the color coating is visible to the practitioner during the use of the guide wire, whereas the portion of the guide wire that is not visible during use is of a traditional color.

In another embodiment of the present invention, the color coding system is applied to the guide wire in the form of a colored band 300 (FIG. 7) proximally positioned about the guide wire between the docking extension and the proximal end. The colored band 300 can be any desired length, with a preferred length of between 1 and 20 centimeters. In this embodiment, a colored polymer with a high adhesion to stainless steel is extruded onto the selected section of guide wire 10. Examples of polymers that can be used to make the color coded band include melt-processable fluoropolymers and polyurethanes. The band 300 is selected from colors that are different from the color of the PTFE coating 20, and preferably stands out in contrast with the existing coating color. Examples of band colors include white, blue, yellow, gold, and teal. The band 300 can be applied by first removing a portion of the existing PTFE coating 20 by laser or other means, and then polishing and/or grinding the bare stainless steel core 22 to create a roughened surface for better polymer adhesion. A silane coating may be applied to further promote polymer adhesion.

The process of applying the band 300 preferably includes grinding the desired section of wire core 22 slightly to ensure that the final diameter of the extruded band 300 is no greater than the diameter of the PTFE coating. Decreasing the core wire diameter will also increase the thickness of the extruded band 300, which may make the band 300 more opaque for a given colorant loading. The grinding process may also have gradual or abrupt tapers or a selected grind profile to aid in the adhesion of the band to the wire core. In an alternative process, the guide wire is jerked rapidly from the extruder once the desired length of polymer is extruded onto the guide wire, as this jerking prevents more polymer from coating onto the wire. The extrusion die assembly may also be modified so that the molten extrusion polymer flows into a cavity between the die and the wire core. Once cooled, the guide wire is jerked out of the extrusion assembly to limit the amount of polymer accumulating on the guide wire. Once the guide wire is removed from the extrusion assembly, excess extruded polymer is removed to make the band length uniform and to expose the docking extension portion of the guide wire. The band 300 may be heated and/or glued to the wire 22 for better adhesion and to prevent ends of the band from protruding above the surface of the PTFE coating, and a lubricious coating may also be applied to the band to minimize catheter interference or frictional sticking points.

For example, standard blue Pellethane 90AE was extruded onto the proximal end of a guide wire to create a marker. The marker adhered well to the guide wire, and the blue polymer was very opaque, although a yellow or gold marker may be even more visible.

In yet another embodiment of the present invention, the color coding of guide wires is accomplished using ultra-short, ultra-intense laser beams (e.g., femtosecond laser) directed to the wire core, altering the surface characteristics of the wire core. The laser forms nanostructures on the surface of the guide wire that affect the way light is absorbed and reflected off the surface. This alteration in the reflection of the light is perceived by humans as a variation in the color of the guide wire core.

Figure 8A:
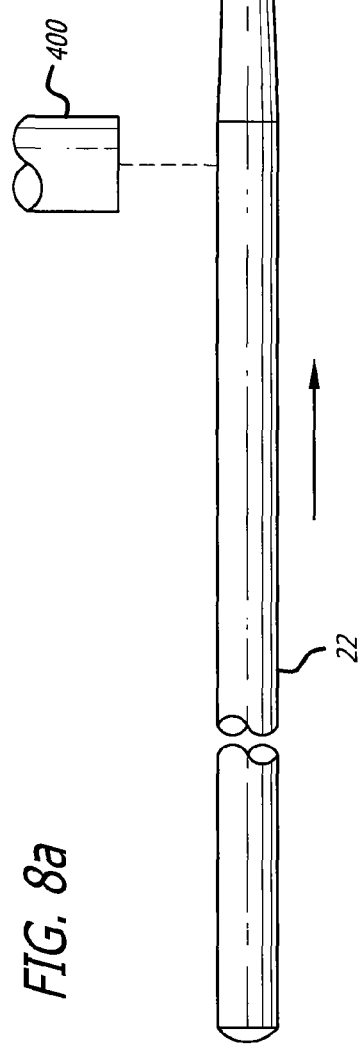
FIGS. 8a and 8b are an elevated perspective view of a laser process for creating nanostructures to a banded surface of a guide wire.
Figure 8B:
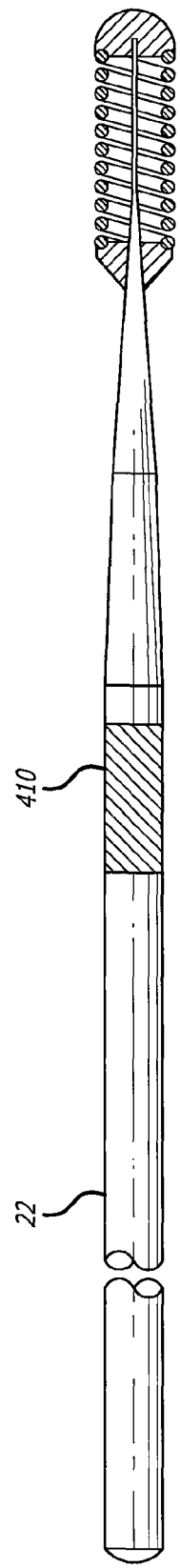
Figure 9:
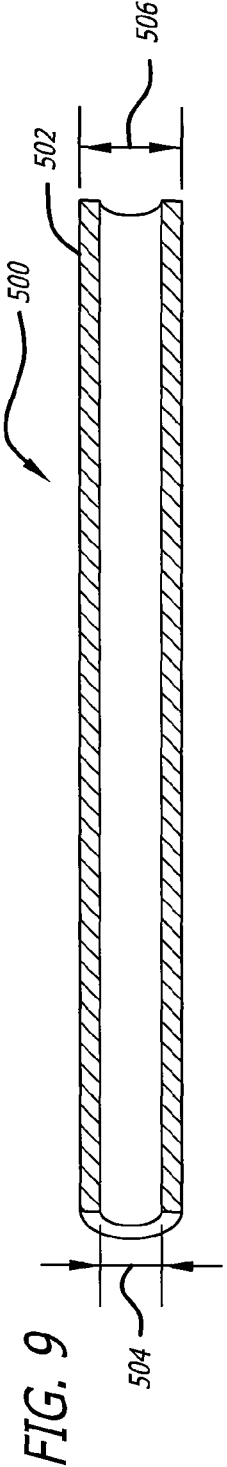
FIG. 9 is a cross-sectional view depicting a color coded tubular sleeve.

In FIG. 8, a laser 400 such as a femtosecond laser is directed toward a guide wire core 22 surface to form nanostructures on the guide wire core surface. The guide wire may be rotated and transversed relative to the laser in order to form a band 410 of modified surface over the length of the guide wire core. The modified band will have a color that is preselected to stand out from the original appearance of the guide wire core to distinguish and differentiate the guide wire from other guide wires having the original appearance. It will be appreciated that various shapes may be produced on the guide wire surface with the desired colors using this process. Also, multiple colors may be achieved using the same laser source without the need for changing the set-up of the apparatus. The laser forms nanostructures on the surface of the wire core such as pits, globules, and strands that modify the optical characteristics of the material. Variation in the laser intensity, pulse length, and number of pulses varies the size and shape of the nanostructures, and thus the appearance of the material. A metallic material such as aluminum can be made to appear gold, for example. Refining the process yields more color options, including almost all desired colors and multicolor appearance such as iridescence.

The advantages of this process include the length of the coloring of the guide wire can be all or partial, depending upon the needs of the user. The process does not involve toxic chemicals and the colors do not dull over time. There are no additional materials that are added to the guide wire. The process eliminates the need for a separate manufacturing and subsequent bonding of colored components, and because the process only affects a small surface layer of the guide wire it does not significantly alter any material properties of the guide wire.

Figure 10:
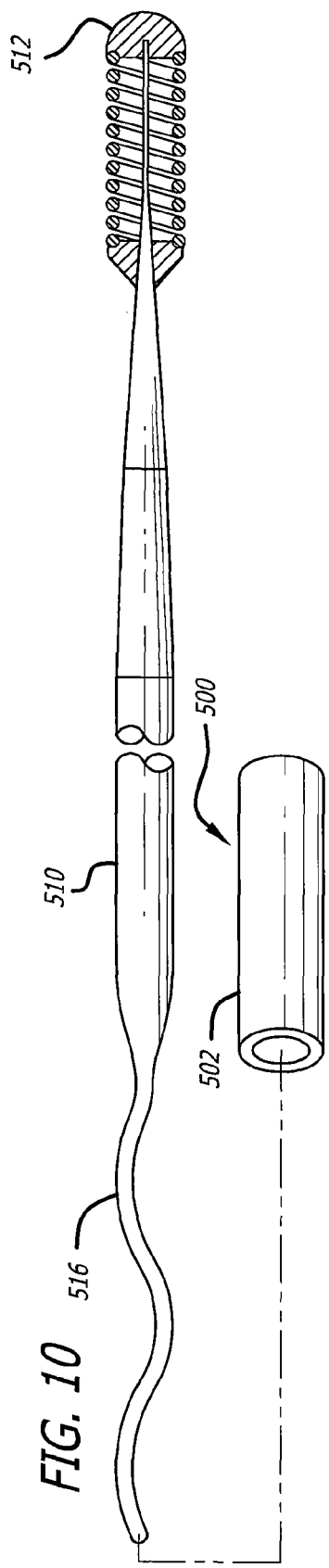
FIG. 10 is a perspective view of a guide wire and a color coded tubular sleeve to be mounted on the guide wire.
Figure 11:
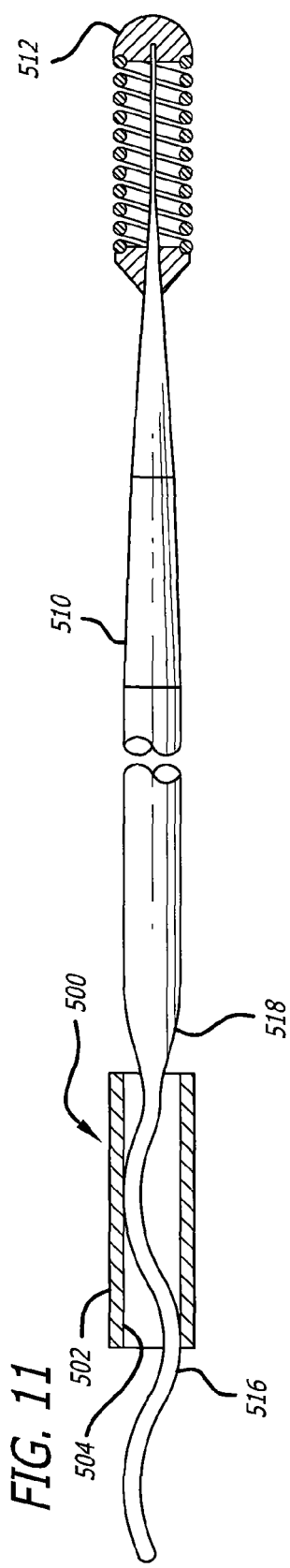
FIG. 11 is a perspective view, partially in section, of a tubular sleeve sliding over the proximal end of a guide wire.
Figure 12:
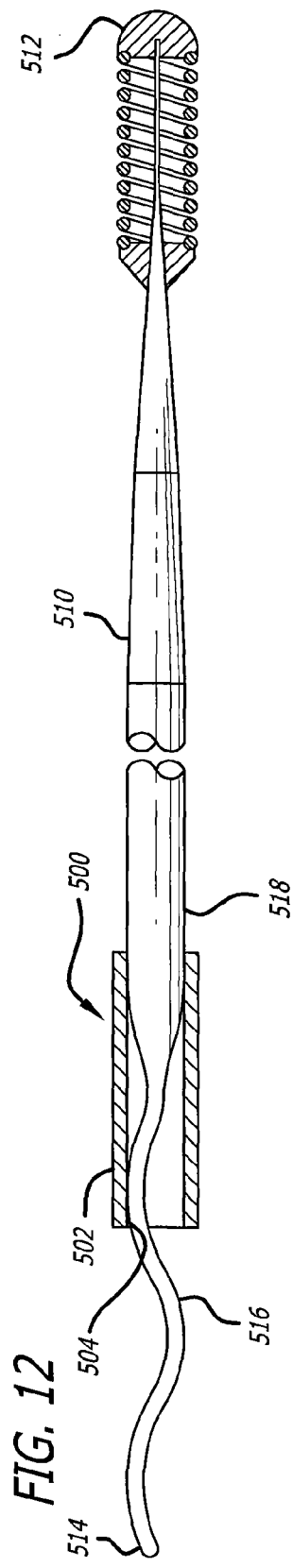
FIG. 12 is a perspective view, partially in section, depicting a color coded tubular sleeve lodged onto the proximal end of a guide wire.

Since more than one guide wire is deployed simultaneously in about 40% of the worldwide percutaneous coronary interventions (PCI), there can be some confusion in identifying between the two guide wires during use. In one embodiment, as shown in FIGS. 9-14, a tubular sleeve 500 has a color coating 502 (or is inherently infused with a color) in order to help identify and distinguish between two guide wires deployed simultaneously. The tubular sleeve 500 has a lumen 504 that extends therethrough and an outer diameter 506 that is sized to approximately match the outer diameter of a guide wire. As shown in FIG. 10, tubular sleeve 500 is sized to slide onto the proximal end 514 of the guide wire assembly. The guide wire assembly includes a distal end 512 having an atraumatic tip which is know in the art. In one embodiment, as shown in FIGS. 10-12, the guide wire assembly 510 has an undulating wire 516 that is used to dock with an extension wire in well known over-the-wire PCI's. The undulating wire 516 is formed by grinding the proximal end 514 of the guide wire 510 in which a tapered proximal section 518 is formed to provide a smooth transition between the guide wire and the undulating wire 516. The undulating wire 516 is sometimes referred to as the "coined" portion of the guide wire assembly 510. In this embodiment, tubular sleeve 500, with color coating 502, slides over the undulating wire 516 and is pushed distally onto the tapered proximal section 518 until the tubular sleeve firmly lodges onto the tapered proximal section. The lumen 504 of the tubular sleeve has a diameter that is greater than the maximum diameter of the undulating wire 516, but is less than the maximum diameter of the tapered proximal section, thereby allowing the tubular sleeve to lodge onto the tapered proximal section as shown in FIG. 12.

During a PCI procedure, when two guide wire assemblies 510 are used simultaneously, the color coded tubular sleeve 500 of one of the guide wires can be removed so that the physician can distinguish between the two guide wires. The tubular sleeve 500 is removed by gripping the sleeve with the fingers and thumb and pulling in a proximal direction thereby sliding the sleeve over the undulating wire 516 and removing it from the guide wire assembly 510. One of the guide wires will have a tubular sleeve 500, and the other guide wire will no longer have a color coded tubular sleeve, thereby the physician can easily distinguish between the two wires during the PCI procedure. If light hand pressure is insufficient to remove a tubular sleeve from the guide wire assembly, a pair of tweezers or small pliers can be used to remove the tubular sleeve.

The color coating 502, or the color of the tubular sleeve 500, can be essentially any color including black, crimson, green, amber, red, yellow, orange, white, blue, gray, or any combination of these colors. It is contemplated that the tubular sleeve 500 be formed from a polymer material that may either already have a specific color, or may be coded with any of the colors identified.

The tubular sleeve 500 is formed from a polymer material that includes fluoropolymer, polyester, Pebax, polyolefin, thermoplastic or thermoset shrink tubing, polyimide, polyethyetherether-keytone (PEEK), or other thermoplastics or thermosets extruded into a tubular form. Further, tubular sleeve 500 can be formed from braided polymer strands made from aramid fibers (e.g., Kevlar), or other pigmented thermoplastics or thermosets. Tubular sleeve 500 also can be formed of a metallic hypotube or foil with or without a color band applied or have a color coating applied by pad printing or ink jet printing. A metallic hypotube also can be colorized by anodizing or using thermal oxidation to produce a color such as straw, amber, blue, dark grey, or black scale coloring. Further, tubular sleeve 500 can be formed from coiled or braided metallic wire or wire ribbon with or without anodizing or oxidizing the metal.

The guide wire assemblies associated with this aspect of the invention generally will have an outer diameter of 0.25 mm (0.010 inch) to 0.45 mm (0.018 inch). The lumen 504 of the tubular sleeve 500 will have a diameter that is smaller than the maximum diameter of the proximal tapered section of the guide wire assembly. The length of the tubular sleeve 500 can range from 2.0 mm (0.08 inch) up to 50.0 mm (2.0 inches). For example, using a guide wire having an outer diameter of 0.35 mm (0.014 inch), a 2.0 mm (0.08 inch) length of tubular sleeve 500 slides over the undulating wire 516 (coined section) and is pushed onto the tapered proximal section 518 of the guide wire until it is firmly lodged onto the tapered proximal section. Alternatively, a length of tubular sleeve 500 slides over the undulating wire 516 and is lodged onto the tapered proximal section 518. Thereafter, any portion of the tubular sleeve extending proximally beyond the undulating wire 516 is trimmed off leaving approximately 0.5 mm (0.02 inch) extending beyond the undulating wire 516 in a proximal direction. The diameter of lumen 504 of the tubular sleeve 500 can range from 0.25 mm (0.01 inch) to 0.26 mm (0.01 inch). Tubular sleeves 500 of the type disclosed herein are commercially available from various manufacturers such as Zeus, Inc. and MicroLumen.

Figure 13:
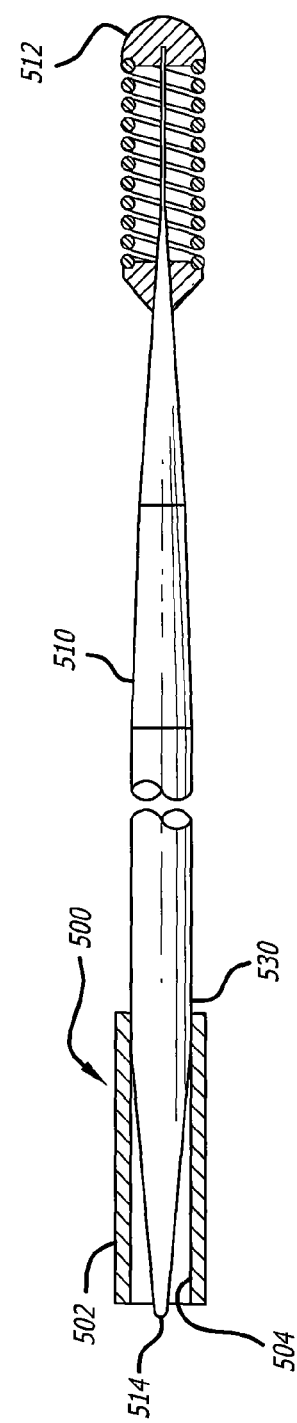
FIG. 13 is a perspective view, partially in section, depicting a color coded tubular sleeve lodged onto the proximal portion of a guide wire.

In another embodiment, as shown in FIG. 13, the guide wire assembly 510 has a distal end 512 and a proximal end 514. In this embodiment, a tapered section 530 is ground onto the proximal end of the guide wire assembly in order to receive a tubular sleeve 500 as previously described. In this embodiment, the tubular sleeve has a color coating 502 and a lumen 504 sized to receive and slide over the tapered section. As previously described, the tubular sleeve 500 is pushed onto the tapered section where it will lodge and firmly attach. The tubular sleeve 500 can be removed using finger pressure or by tweezers or small pliers as previously described. In this embodiment, the length of tubular sleeve 500 can range from 2.0 mm (0.08 inch) to 50.0 mm (2.0 inches), and a portion of the tubular sleeve may extend beyond the proximal end 514 by approximately 0.5 mm (0.02 inch).

Figure 14:
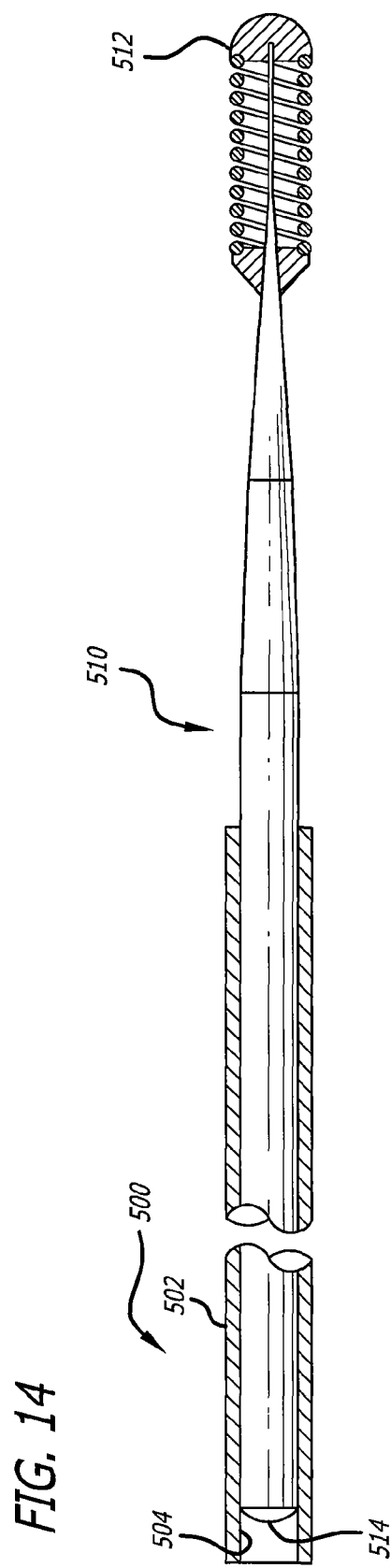
FIG. 14 is a perspective view, partially in section, depicting a tubular sleeve lodged onto the proximal portion of a guide wire.

In another embodiment, as shown in FIG. 14, a guidewire assembly 510 has a distal end 512 and a proximal end 514. A tubular sleeve 500 has a color coating 502 and a lumen 504 sized to allow the tubular sleeve to slide over the guide wire assembly 510. The tubular sleeve 500 will have a tight or snug fit on the guide wire assembly so that it is not easily removed, but can be removed when two guide wires are used simultaneously and one of the tubular sleeves is removed so that the physician can distinguish between the two guide wires. In this embodiment, the tubular sleeve can have a length ranging from 2.0 mm (0.08 inch) to 50.0 mm (2.0 inches), and approximately 0.5 mm (0.02 inch) of the tubular sleeve can extend beyond the proximal end 514 of the guide wire assembly 510. In this embodiment, the color coded tubular sleeve can be positioned anywhere along the proximal 50 cm (19.7 inches) of the guide wire.

It is to be understood that the foregoing description is intended to be illustrative of embodiments of the present invention but is not intended to be limiting in any manner. One of ordinary skill in the art will readily appreciate modifications and alterations to the above described examples, and the intention includes all such modifications and alterations. Accordingly, the scope of the invention is properly interpreted to be encompassed by the words of the appended claims, using the words' ordinary meaning, without limiting the definition of those words to the examples provided herein.

What is claimed:

1. A guide wire for use in a medical procedure having an elongate core, a flexible distal tip, and a low friction outer coating, the guide wire comprising:
   a color coding mechanism for distinguishing the guide wire from similar guide wires, wherein the elongate core is made of stainless steel and the color coding mechanism comprises a thickened chromium oxide film on a proximal end and a distal end of the elongate core and having optical characteristics that are distinguishable from an elongate core without the thickened chromium oxide film; and
   the low friction outer coating extends along the entire elongate core except for a 5 to 20 cm proximal portion of the elongate core.

2. The guide wire of claim 1, wherein the thickened chromium oxide film is formed by an electrochemical process.

3. The guide wire of claim 2, wherein the thickened chromium oxide film gives the elongate core a color selected from bronze, purple, blue, red, black, and green.

4. The guide wire of claim 2, wherein the low friction outer coating is polytetrafluoroethylene.

5. The guide wire of claim 4, wherein the low friction outer coating is transparent, enabling the thickened chromium oxide layer to be viewed through the outer coating.

6. The guide wire of claim 1, wherein the color coding mechanism comprises a sputtered layer of a colored material onto the elongate core.

7. The guide wire of claim 1, wherein the color coding mechanism comprises a plated layer of a colored material onto the elongate core.

8. The guide wire of claim 1, wherein the color coding mechanism comprises a painted layer of a colored material onto the elongate core.

9. The guide wire of claim 1, wherein the color coding mechanism contributes to a resistance of the guide wire to corrosion.

10. The guide wire of claim 2, wherein the elongate core with the thickened chromium oxide film extends proximally outside the low friction outer coating.

11. The guide wire of claim 1, wherein a portion of the low friction outer coating is removed to expose a portion of the color coding mechanism.

12. The guide wire of claim 11, wherein the exposed portion of the color coding system serves as a marker for positioning the guide wire.

13. The guide wire of claim 1, wherein the color coding mechanism comprises a colored portion of a wire core attached to a proximal end of the guide wire.

14. The guide wire of claim 1, wherein the color coding mechanism is located on the low friction outer coating.

15. The guide wire of claim 14, wherein the low friction outer coating comprises PTFE, and a color of the PTFE constitutes the color coding mechanism.

16. The guide wire of claim 15, wherein the color of the PTFE is selected from a group comprising blue, white, yellow, and gold.

17. The guide wire of claim 14, wherein the low friction outer coating is applied via a spray process where a spray of a non-standard color is applied to the guide wire.

18. The guide wire of claim 17, further comprising a removable mask on the guide wire that can be removed after the spraying process to leave an uncolored portion of the guide wire.

19. The guide wire of claim 18, where the uncolored portion of the guide wire is positioned to serve as a marker for use in positioning the distal end of the guide wire.

20. The guide wire of claim 14, where the color coding mechanism is located solely between a docking extension and a proximal end of the guide wire.

21. The guide wire of claim 1, wherein the color coding mechanism comprises a colored band placed over the elongate core.

22. The guide wire of claim 21, wherein the colored band is formed from an extruding process.

23. The guide wire of claim 21, wherein the colored band is located between a docking extension and a proximal end of the guide wire.

24. The guide wire of claim 21, wherein the colored band has a color selected from a group of white, blue, yellow, gold, and teal.

25. The guide wire of claim 21, further comprising a roughened surface of the elongate core adjacent a surface of the colored band.

26. The guide wire of claim 21, wherein an outer diameter of the colored band is no greater than an outer diameter of the low friction outer coating.

27. The guide wire of claim 21, further comprising a layer of silane between the elongate core and the colored band.

28. The guide wire of claim 21, further comprising an adhesive material disposed between the colored band and the elongate core.

29. The guide wire of claim 1, wherein the color coding mechanism comprises laser-induced microstructures formed on a surface of the elongate core to alter a color of the elongate core.

30. The guide wire of claim 29, wherein a preselected area of the guide wire is visually altered by the laser induced microstructures.

31. A method for color coding a guide wire for use in a medical procedure, comprising:
   providing a flexible, metallic core member having a proximal end and a distal end;
   exposing the proximal end and the distal end of the metallic core member to a heated acidic solution;
   applying an electrical current to the metallic core member while exposed to the heated acidic solution to alter a color of the proximal end and the distal end of the metallic core member; and
   applying a low friction outer coating to the metallic core member while leaving a proximal portion of 5 to 20 cm of the metallic core member uncoated.

32. The method of color coding a guide wire of claim 31, wherein the proximal portion of the metallic core member that is uncoated is a proximal end of the metallic core member.

33. The method of color coding a guide wire of claim 31, wherein the metallic core member is made of stainless steel, and the altering of the color of the metallic core member is a result of a thickened chromium oxide layer.

34. The method of color coding a guide wire of claim 31, wherein the low friction outer coating applied to the metallic core member is transparent.

35. The method of color coding a guide wire of claim 31, wherein the color of the metallic core member after the applied electrical current is selected from a group comprising gold, bronze, purple, blue, red, black, and green.

36. The method of color coding a guide wire of claim 31, further comprising removing a portion of the low friction outer coating to expose a portion of the metallic core member with the altered color.

37. The method of color coding a guide wire of claim 36, further comprising selecting a position for removing a portion of the low friction outer coating such that the position can be used as a marker for positioning the guide wire inside a body lumen.

38. The method of color coding a guide wire of claim 31, further comprising applying a silicone based film to the elongate core member before applying the low friction outer coating.

* * * * *